(12) United States Patent
Belous et al.

(10) Patent No.: US 9,113,624 B2
(45) Date of Patent: Aug. 25, 2015

(54) SYSTEM AND METHOD FOR PERFUSING BIOLOGICAL ORGANS

(75) Inventors: Anna Belous, Longmont, CO (US); Tom E. McMunigal, Mead, CO (US); Ronald J. Podhajsky, Boulder, CO (US); Jeffrey A. Hammond, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1043 days.

(21) Appl. No.: 12/251,857

(22) Filed: Oct. 15, 2008

(65) Prior Publication Data

US 2010/0092939 A1  Apr. 15, 2010

(51) Int. Cl.
*A01N 1/00* (2006.01)
*A01N 1/02* (2006.01)

(52) U.S. Cl.
CPC .............. *A01N 1/0247* (2013.01); *A01N 1/02* (2013.01); *A01N 1/0226* (2013.01)

(58) Field of Classification Search
CPC .............................. A01N 1/0247; A01N 1/02
USPC ................. 35/284.1; 435/1.2, 284.1
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,469,103 A | 9/1984 | Barrett | |
| 4,572,190 A | 2/1986 | Azam et al. | |
| 4,745,759 A * | 5/1988 | Bauer et al. | 435/284.1 |
| 4,798,215 A | 1/1989 | Turner | |
| 5,024,668 A | 6/1991 | Peters et al. | |
| 5,030,575 A * | 7/1991 | Stofac | 435/284.1 |
| 5,097,844 A | 3/1992 | Turner | |
| 5,417,210 A | 5/1995 | Funda et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Peristaltic Pump Tubing, Spectrum Chromatography. Web Archive <http://web.archive.org/web/20060206084312/http://www.lplc.com/tubing/pumptube.html> (Feb. 6, 2006).*

(Continued)

*Primary Examiner* — Michael Hobbs
*Assistant Examiner* — Liban Hassan

(57) ABSTRACT

A system for perfusing a biological organ for use as an experimental model includes a housing having sides that define a cavity for containing a biological organ model within a solution. The housing includes a plurality of apertures defined therethrough configured to mechanically interface with a filter, one or more heating elements and one or more sensors. A peristaltic pump is configured to withdraw and pressurize the solution from the housing and reintroduce the solution under pressure into the biological organ. A heat control module operatively connects to the heating elements and is configured to regulate the temperature of the solution within the housing. A data acquisition system operatively connects to the heat control module, the peristaltic pump and the sensor(s) and regulates and monitors the pressure, flow rate and temperature of the solution during electrical treatment of the biological organ.

12 Claims, 3 Drawing Sheets

(56) References Cited

U.S. PATENT DOCUMENTS

| | | | |
|---|---|---|---|
| 5,723,282 A * | 3/1998 | Fahy et al. | 435/1.3 |
| 6,031,375 A | 2/2000 | Atalar et al. | |
| 6,375,606 B1 | 4/2002 | Garibaldi et al. | |
| 6,477,426 B1 | 11/2002 | Fenn et al. | |
| 6,603,994 B2 | 8/2003 | Wallace et al. | |
| 6,666,860 B1 | 12/2003 | Takahashi | |
| 6,666,862 B2 | 12/2003 | Jain et al. | |
| 6,725,080 B2 | 4/2004 | Melkent et al. | |
| 6,788,977 B2 | 9/2004 | Fenn et al. | |
| 6,974,463 B2 | 12/2005 | Magers et al. | |
| 7,439,736 B2 | 10/2008 | Meaney et al. | |
| 7,467,015 B2 | 12/2008 | Van der Weide | |
| 7,565,207 B2 | 7/2009 | Turner et al. | |
| 2002/0022836 A1 | 2/2002 | Goble et al. | |
| 2003/0086830 A1 * | 5/2003 | Haywood et al. | 422/102 |
| 2004/0058432 A1 * | 3/2004 | Owen et al. | 435/284.1 |
| 2004/0097805 A1 | 5/2004 | Verard et al. | |
| 2004/0170950 A1 * | 9/2004 | Prien | 435/1.2 |
| 2004/0229348 A1 * | 11/2004 | Kahlert et al. | 435/293.1 |
| 2004/0242992 A1 | 12/2004 | Hareyama | |
| 2005/0255442 A1 * | 11/2005 | Brassil et al. | 435/1.2 |
| 2006/0030914 A1 | 2/2006 | Eggers et al. | |
| 2006/0154358 A1 * | 7/2006 | Hassanein et al. | 435/284.1 |
| 2006/0166360 A1 * | 7/2006 | Berthiaume et al. | 435/366 |
| 2007/0049915 A1 * | 3/2007 | Haemmerich et al. | 606/32 |
| 2007/0084222 A1 * | 4/2007 | Voute et al. | 62/66 |
| 2008/0017194 A1 * | 1/2008 | Hassanein et al. | 128/200.24 |
| 2008/0183165 A1 | 7/2008 | Buysse et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |

OTHER PUBLICATIONS

Spectrum Chromatography, "Laboratory and Peristaltic Pump Tubing", Mar. 1999.*
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.

(56) References Cited

OTHER PUBLICATIONS

U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw-Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. I 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.

(56) References Cited

OTHER PUBLICATIONS

Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(2005.03); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite•Element Codes to Model Electrical Heating and Non•Llnear Thermal Transport in Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et aI., "Accidental Bums", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.

(56) References Cited

OTHER PUBLICATIONS

European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

SYSTEM AND METHOD FOR PERFUSING BIOLOGICAL ORGANS

BACKGROUND

The present disclosure relates to a system and method for modeling the heat loss of an organ during energy-based ablation treatments. More particularly, the present disclosure relates to a bench-top, perfusion system and methods for simulating heat loss of a liver during radiofrequency and/or microwave ablation procedures.

TECHNICAL FIELD

In the treatment of diseases such as cancer, certain types of cancer cells have been found to denature at elevated temperatures that are slightly lower than temperatures normally injurious to healthy cells. Known treatment methods, such as hyperthermia therapy, use electrosurgical energy (e.g., electromagnetic radiation) to heat diseased cells to temperatures above 41° C. while maintaining adjacent healthy cells below the temperature at which irreversible cell destruction occurs. These methods involve applying electrosurgical energy to heat, ablate and/or coagulate tissue. Radiofrequency (RF) or Microwave energy is sometimes utilized to perform these procedures.

Treatment may involve inserting ablation probes into tissues or organs where cancerous tumors have been identified. Once the probes are positioned, electrosurgical energy is passed through the probes into surrounding tissue which heats to a certain temperature to destroy malignant tissue. There are a number of different types of apparatus that can be used to perform ablation procedures. Typically, microwave apparatus for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator. RF probes may also be utilized to accomplish the same or similar purposes.

Energy is typically applied via antenna assemblies that penetrate tissue. For example and with particular respect to microwave energy probes, several types of antenna assemblies are known, such as monopole and dipole antenna assemblies. In monopole and dipole antenna assemblies, microwave energy generally radiates perpendicularly away from the axis of the conductor. A monopole antenna assembly includes a single, elongated conductor that transmits microwave energy. A typical dipole antenna assembly has two elongated conductors, which are linearly aligned and positioned end-to-end relative to one another with an electrical insulator placed therebetween. Each conductor may be about ¼ of the length of a wavelength of the microwave energy, making the aggregate length of the two conductors about ½ of the wavelength of the supplied microwave energy. During certain procedures, it can be difficult to assess the extent to which the microwave energy will radiate into and heat the surrounding tissue, making it difficult to determine the area or volume of surrounding tissue that will be ablated. In addition, in certain instances it may also be difficult to assess the extent to which heat is lost inside the tissue or organ during the ablation procedure.

SUMMARY

The present disclosure relates to a system for perfusing a biological organ, e.g., a liver, for use as an experimental model and includes a housing having sides that define a cavity for containing a biological organ model within a solution. The housing includes a plurality of apertures defined therethrough configured to mechanically interface with one or more heating element and/or one or more sensors. One or more filters may also be mechanically interfaced with the apertures. A peristaltic pump is included and configured to withdraw and pressurize the solution from the housing and reintroduce the solution under pressure into the biological organ. A heat control module is configured to regulate the temperature of the solution within the housing and a data acquisition system controls and monitors the heat control module, the peristaltic pump and the sensor(s) to monitor the pressure, flow rate and temperature of the solution during electrical treatment of the biological organ. The sensor may be a pressure transducer, thermocouple or flow rate monitor.

In one embodiment, a conductive ground plate may be disposed in the housing and configured to provide a return path during radio frequency electrical treatment of the biological organ. The ground plate may be selectively removed for cleaning and/or replacement purposes. A specimen table may also be included for supporting the biological organ within the housing. The specimen table may be configured to nestingly-receive the ground plate. The specimen table may also include perforations to allow the solution to freely circulate around the biological organ when disposed in the housing.

In one embodiment, the data acquisition system includes a computer for analyzing data received from the sensor, the heat control module and/or the peristaltic pump. In yet another embodiment, the peristaltic pump includes pressurized tubes for supplying solution to the biological organ, e.g., a liver, each tube configured to accommodate an entry vessel of the liver, e.g., about 0.8 centimeters in diameter for the tube attached to the portal vein and about 0.2 centimeters in diameter for the tube attached to the hepatic artery. The differently sized tubes create a subdivided flow ratio of about 70:30 between the portal vein and hepatic artery. The peristaltic pump may be configured to create a flow rate of about 1500 ml/min. through the liver.

In still another embodiment, the solution includes saline, heparin or other commonly used blood substitutes. The system may also include one or more filters configured to reduce blood clots within the circulating solution. Yet in another embodiment, the system includes an electrode holder for supporting one or more electrodes during electrical activation thereof.

The present disclosure also relates to a method for perfusing a biological organ (e.g., a liver) and includes the initial step of flushing blood from the biological organ utilizing one or more commonly known flushing procedures, e.g., utilizing a saline flushing solution or a saline and Heparin flushing solution (or other commonly known solution) to prevent or clear clotting (e.g., coagulation of smaller capillaries in the liver). The method also includes the steps of: placing the biological organ into a housing containing a perfusing solution; pumping the solution from the housing and reintroducing the solution under pressure into the biological organ through one or more natural orifices; regulating the temperature of the solution (via one or more heating elements and sensors) with a heat control module; and acquiring data relating to the pressure, flow rate and temperature of the solution during electrical treatment of the biological organ.

In an additional step, the solution may be filtered prior to entering the biological organ. With particular respect to a liver used as a biological organ, the pump may be configured to produce a flow rate of 1500 ml/min. into the liver with a ratio of about 70:30 portal vein to hepatic artery. The heating elements may be utilized to maintain the solution at a temperature of about 37 degrees Celsius.

BRIEF DESCRIPTION OF THE DRAWINGS

Various embodiments of the subject instrument are described herein with reference to the drawings wherein.

DETAILED DESCRIPTION

Prior to perfusing a biological organ, e.g., a liver 500, for use in gathering heat loss and other experimental data from the liver 500 during an ablation treatment, the liver 500 is initially flushed of blood utilizing one or more suitable flushing procedures utilizing a saline solution or a saline and Heparin solution to prevent clotting (e.g., coagulation of smaller capillaries in the liver).

Figure 1:
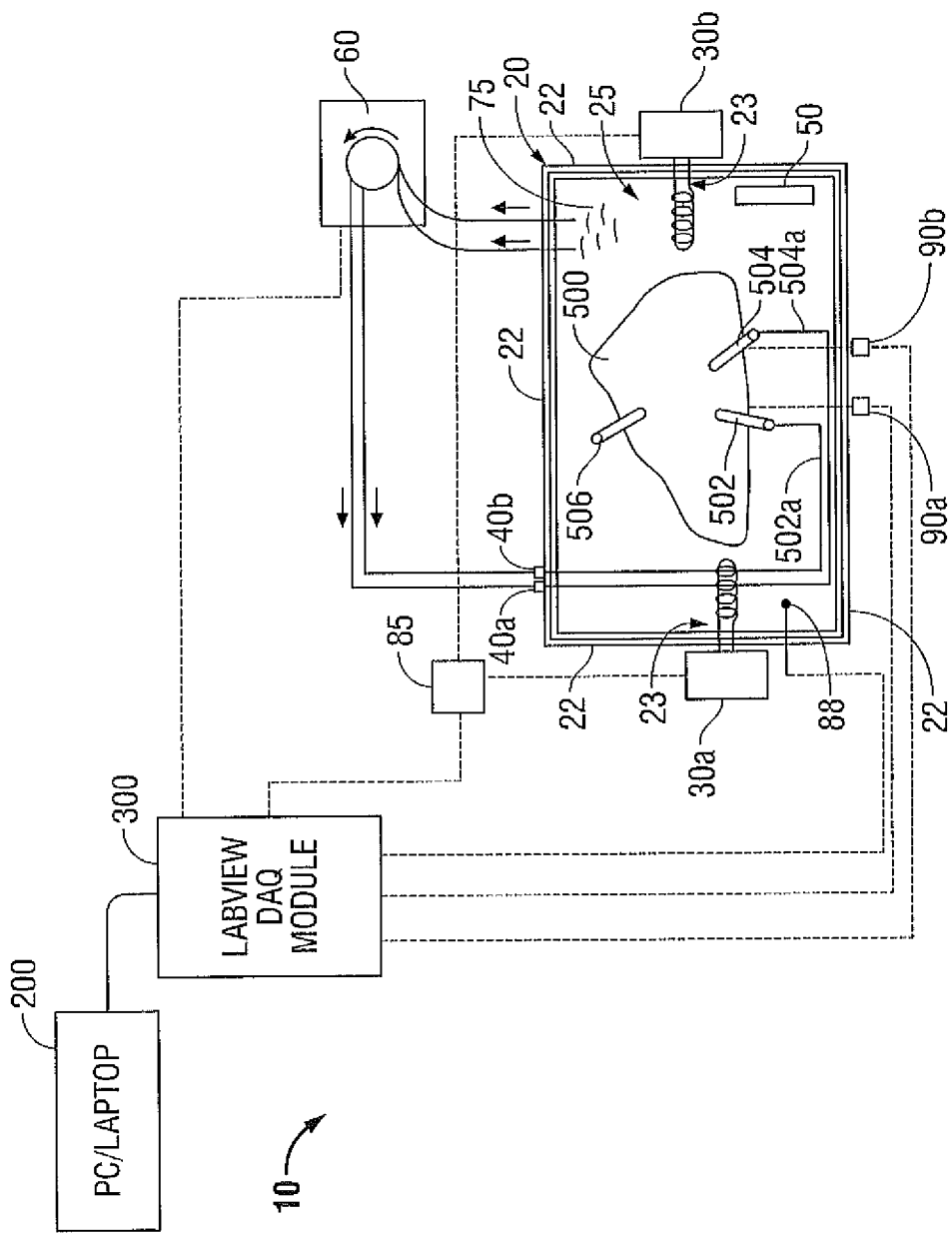
FIG. 1 is a schematic representation of a biological organ perfusion system shown according to one embodiment of the present disclosure.

Referring initially to FIG. 1, a schematically-illustrated system 10 for perfusing a biological organ, e.g., liver 500, is depicted and generally includes a housing 20 having sides 22 that are configured to define a cavity 25 for supporting or containing a liver 500 or other biological tissue therein. The housing 20 acts as a reservoir for containing the liver 500 in a solution 75 (e.g., saline or other suitable liquid of about 30 liters). The housing 20 includes a series of ports 23 defined through one or more of the sides 22 that are configured to operatively couple to one or more mechanical components utilized in the perfusing system 10, e.g., heaters 30a and 30b, fittings with valves 40a and 40b and conductive ground pad 50.

A peristaltic pump 60 is configured to operatively couple to the system 10 and supplies solution 75 (e.g., a saline solution) for infusion into the liver 500. The pump 60 draws solution 75 from a reservoir contained within the cavity 25 for circulation purposes. Solution 75 is drawn from the reservoir into the pump 60, which forces the solution 75 into the liver 500 through one or more vein and/or artery entry points in the liver 500, e.g., the portal vein 502 and/or the hepatic artery 504. The average rate of blood flow through a typical liver is about 1500 ml/min. with the majority of blood flowing through the portal vein (e.g., about 70%). In the present disclosure, the fluid perfuses the liver 500 under about the same flow rate and is forced to exit through the vena cava 506 into the reservoir where it is, again, re-circulated to the pump 60.

In order to simulate blood flow in the perfusing system 10 under real conditions, the tubing 502a and 504a of the perfusing system 10 is adapted to accommodate the different diameter size of the two blood vessels 502 and 504, respectively. For example, the tubing diameter for the portal vein 502 may be nominally sized to about 0.8 cm and the tubing diameter size for the hepatic artery may be sized to about 0.2 cm. The different tubing diameters and the multi-channel or multi-port peristaltic pump 60 establish adjustable flow rates to simulate a working liver model similar to live human liver.

As one example, a working pump rate at 280 RPM creates about a 1500 ml/min flow through a model liver 500 and the different diameter tubing sizes allows a subdivided flow of about 70% portal vein and 30% hepatic artery.

In one embodiment, the temperature of the solution 75 is regulated using one or more heaters 30a and 30b, and various controls 85 and 300 and sensors 88 operably connected to the perfusing system 10. For example and as best shown in FIG. 1, the perusing system 10 includes two heaters 30a and 30b coupled to a heat control module 85 for controlling the temperature of the saline solution 75. The heat control module 85, in turn, communicates with one or more thermocouples 88 to sense the temperature of the saline solution 75 in the reservoir and actively adjust the heaters to maintain the reservoir temperature at about 37° C. The thermally regulated saline that perfuses the liver dictates the temperature of the organ nominally at 37° C. Other suitable temperatures are contemplated by the present disclosure. As described in more detail below with respect to FIGS. 2 and 3, various mounting blocks may be utilized to support the thermocouple(s) 88 and heaters 30a and 30b. The heaters 30a and 30b may be directly coupled to one or more sides of the housing 120 or supported upon a support table 170 disposed adjacent the perfusing system 10.

The perfusing system 10 may also be equipped with one or more sensors or transducers 90a and 90b that are configured to monitor the pressure, flow rate and/or temperature in the portal vein 502 and/or the hepatic artery 504. The measured values are communicated back to a computer 200 and/or a data acquisition system 300 that actively monitors, records and/or regulates the various operating and control elements of the perfusing system 10, e.g., heaters 30a and 30b, pump 60, sensors 90a and 90b, thermocouple(s) 88. This enables an operator to vary certain parameters of the perfusing system 10 to simulate various conditions. The valves 40a and 40b may be regulated as well to control the flow of fluid into the system. The control conditions are highly controllable and highly repeatable with limited variability in the testing environment. This enables an operator to test liver reaction and liver response under consistent operating conditions with minimal variation amongst the pre-set operating parameters. The system 10 also enables the operator to vary certain parameters, e.g., temperature, pressure, etc., while maintaining other parameters fixed for experimental purposes.

Figure 2:
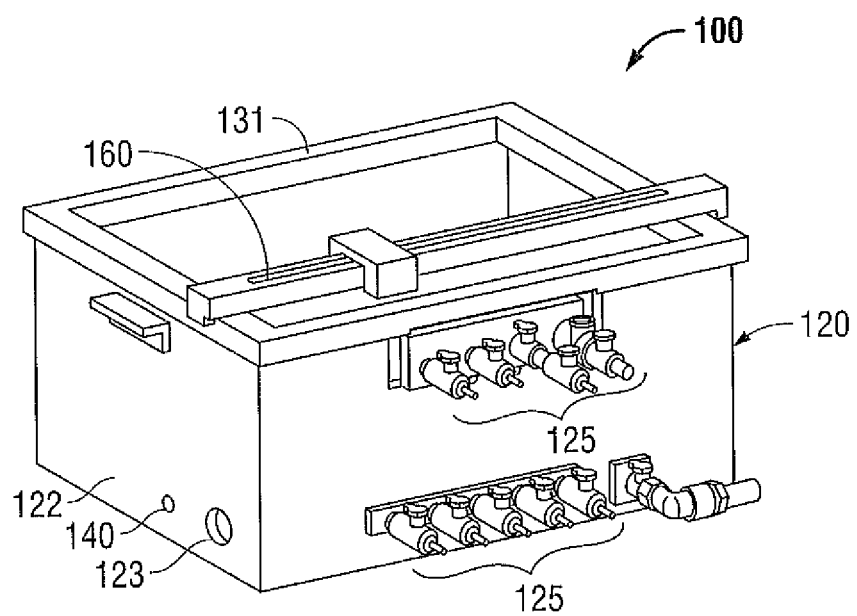
FIG. 2 is an enlarged, perspective model view of a biological organ perfusion system according to another embodiment of the present disclosure.
Figure 3:
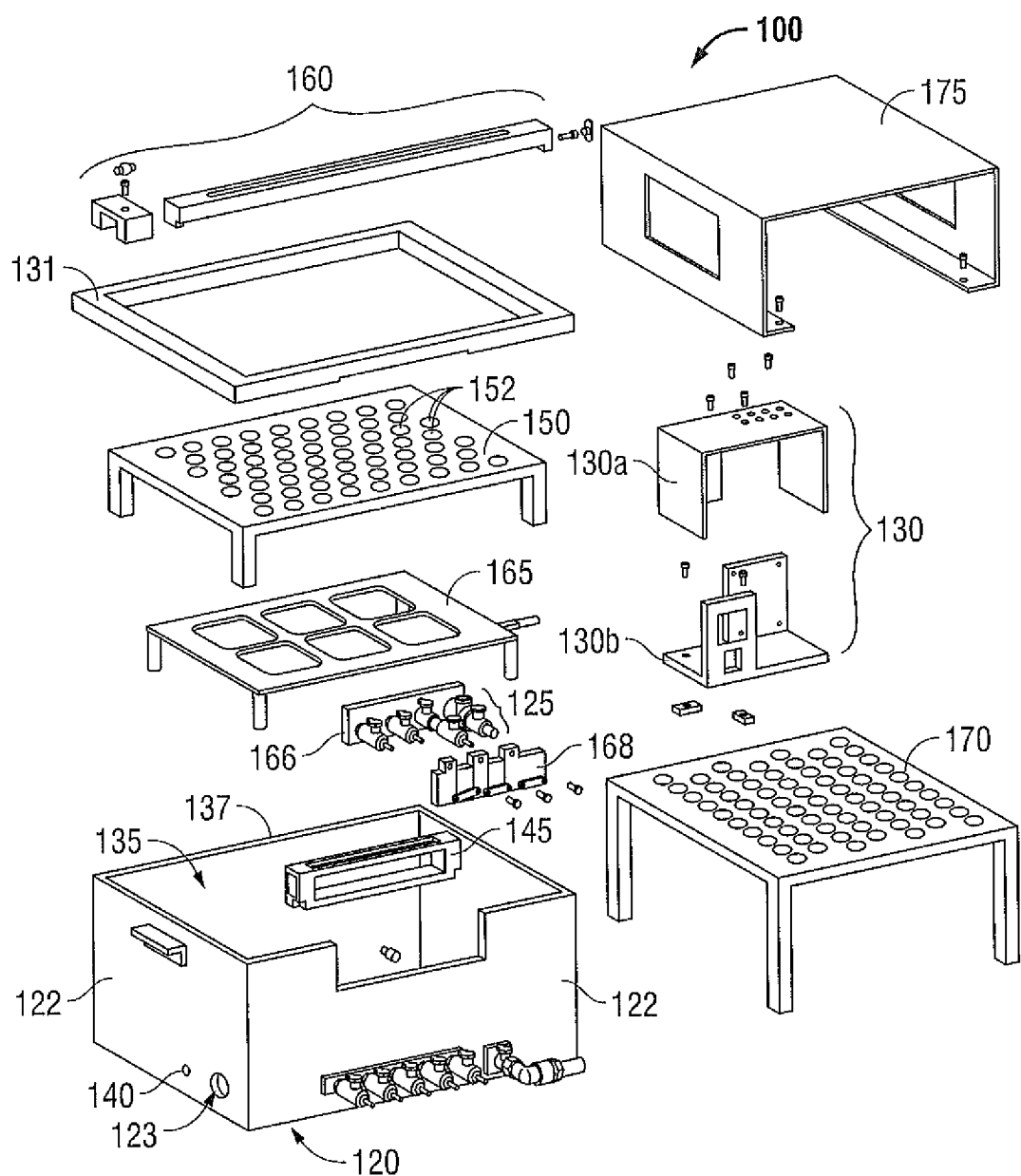
FIG. 3 is an enlarged, exploded view of the biological organ perfusion system of FIG. 2.

FIGS. 2 and 3 show a working model representation of a liver perfusion system 100 in accordance with the schematic embodiment of the present disclosure shown in FIG. 1. More particularly, the liver perfusing system 100 includes a non-conductive housing 120 having sides 122 that form an internal cavity 135 for containing a saline solution 75 or other suitable solution as mentioned above (See FIG. 1). The system 100 is designed as a modular unit with selectively adjustable and removable components, which permits more adaptability of the system to simulate working conditions.

The sides 122 of the housing 120 are configured with various mechanical interfaces, e.g., apertures or ports 123, slits, cutouts 121, ridges 137, etc., that allow the user to easily mount and/or couple the various components that make up the system 100, e.g., filters or valves 125, thermocouples 88, lid 131 and electrode holder assembly 160, etc. For example, a slit 121 is defined in a side 122 of the housing 120 and is dimensioned to matingly receive a filter block 145 for supporting one or more filters or filter valves 125 thereon; fitting block 166 may be utilized to support a plurality of filters or valves 125 within the filter block 145 mounted to the inside of housing 120.

In another example, a heater control box mount 130 may be coupled atop table 170 to support a heater, e.g., heater 30a, 30b (See FIG. 1) thereon for regulating the temperature of the solution 75 (See FIG. 1) inside the housing 120. The heater control box 130 also prevents the temperature controller (heater 30a and 30b) from accidental exposure to the solution 75. Moreover, one or more thermocouple ports 140 may be defined in one or more sides 122 of the housing 120 to mount or support thermocouples 88 (See FIGS. 1 and 3) that monitor the temperature of the solution 75 and provides information relating thereto back to the heat control module 85 (See FIG. 1). A removable thermocouple block 168 may also be employed to support an array or series of thermocouples 88 and other sensors (not shown) utilized with the system 100 within the thermocouple port(s) 140. The various mounts 130 and support blocks 145, 168 are all selectively removeably to facilitate cleaning and/or replacement of accessories.

The housing 20 is configured to accommodate a specimen table 150 therein that supports the treatment specimen, e.g., liver 500. The specimen table 150 includes perforations 152 to facilitate circulation of the solution 75 around the liver 500. Conductive ground plate 165 is disposed in the housing 120 below the specimen table 150 in a nested-like arrangement and may be dimensioned to connect to a ground plug (not shown) that connects through the housing 120. Conductive ground plate 165 provides return path back to the electrosurgical generator (not shown) during electrical activation. The conductive ground plate 165 simulates the ground return for radiofrequency applications but can easily be removed during microwave ablation. An accessory table 170 and computer shelf 175 may also be utilized to support various electronic accessories proximate the system 100.

In use the liver perfusion system 10 (or 100) may be utilized to regulate, monitor and/or adjust the pressure, flow rate and temperature of the solution 75 flowing into the hepatic artery 504 and portal vein 502, through the liver 500 and out the vena cava 506 The system 10 (or 100) allows for a highly repeatable and highly controllable testing environment for modeling heat loss within a liver 500 during the application of electrical energy, such as microwave ablation or radiofrequency application.

The present disclosure also relates to a method for perfusing a biological organ (e.g., a liver 500) and includes the initial step of flushing blood from the biological organ 500 utilizing one or more commonly known flushing procedures utilizing a saline flushing solution or a saline and Heparin flushing solution to prevent clotting (e.g., coagulation of smaller capillaries in the liver). The method also includes the steps of: placing the biological organ 500 into a housing 20 containing a solution 75; pumping the solution 75 from the housing 20 and reintroducing the solution 75 under pressure into the biological organ 500 through a natural orifice (e.g., in the case of a liver the portal vein 502 or hepatic artery 504); regulating the temperature of the solution 75 with the housing 20 utilizing one or more heating elements 30a and 30b and sensors 90a, 90b, 88 that are regulated and monitored with a heat control module 85; and acquiring data relating to the pressure, flow rate and temperature of the solution 75 during electrical treatment of the biological organ 500.

In an additional step, the solution 75 is filtered prior to entering the biological organ 500. The pump 60 of the pumping step may be configured to produce a flow rate of about 1500 ml/min. into the biological organ 500 with a ratio of about 70:30 portal vein to hepatic artery. Other pumping speeds and flow rates are also contemplated depending upon a particular purpose or when perfusing a particular organ. One or more heating elements 30a and 30b may be utilized to maintain the solution 75 at a temperature of about 37 degrees Celsius.

From the foregoing and with reference to the various figure drawings, those skilled in the art will appreciate that certain modifications can also be made to the present disclosure without departing from the scope of the present disclosure. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A system for perfusing a biological organ for use as an experimental model, the system comprising:
   a housing having sides that define a cavity for containing a biological organ within a solution, the housing including a plurality of apertures defined therethrough configured to mechanically interface with at least one heating element and at least one sensor;
   a removable conductive ground plate disposed in the housing, the removable conductive ground plate including a plurality of legs extending therefrom and configured to provide a return path during radiofrequency electrical treatment of the biological organ;
   a specimen table for supporting the biological organ within the housing, the specimen table including a plurality of legs extending therefrom and configured to nestingly-receive the removable conductive ground plate below the specimen table;
   a peristaltic pump configured to withdraw the solution from the housing and reintroduce the solution under pressure into the biological organ;
   a heat control module operatively connected to the at least one heating element, the heat control module configured to regulate the temperature of the solution within the housing; and a data acquisition system operatively connected to the heat control module, the peristaltic pump and the at least one sensor, the data acquisition system configured to regulate the pressure, flow rate and temperature of the solution during electrical treatment of the biological organ, the data acquisition system includes a computer for analyzing data received from the at least one sensor, heat control module and peristaltic pump.

2. The system for perfusing a biological organ according to claim 1, wherein the at least one sensor includes at least one of a pressure transducer, thermocouple, and flow rate monitor.

3. The system for perfusing a biological organ according to claim 1, wherein the specimen table includes perforations configured to allow the solution to freely circulate around the biological organ.

4. The system for perfusing a biological organ according to claim 1, wherein the peristaltic pump includes pressurized tubes for supplying solution to the biological organ, each pressurized tube configured to accommodate an entry vessel of the biological organ.

5. The system for perfusing a biological organ according to claim 4, wherein the biological organ is a liver and the pressurized tube attached to a portal vein of the liver is about 0.8 centimeters in diameter and the pressurized tube attached to a hepatic artery of the liver is about 0.2 centimeters in diameter.

6. The system for perfusing a biological organ according to claim 1, wherein the biological organ is a liver and the peristaltic pump creates a flow rate of about 1500 ml/min. through the liver.

7. The system for perfusing a biological organ according to claim 5, wherein the differently sized pressurized tubes create a subdivided flow ratio of about 70:30 between the portal vein and hepatic artery.

8. The system for perfusing a biological organ according to claim 1, wherein the solution includes saline.

9. The system for perfusing a biological organ according to claim 1, wherein the solution includes heparin.

10. The system for perfusing a biological organ according to claim 1, wherein one of the plurality of apertures defined through the housing is dimensioned to matingly receive a filter block mounted within the housing, the filter block including at least one filter configured to reduce blood clots within the solution.

11. The system for perfusing a biological organ according to claim 1, further comprising an electrode holder for supporting at least one electrode during electrical activation thereof.

12. The system for perfusing a biological organ according to claim 3, wherein the removable conductive ground plate includes a plurality of openings defined therein.

* * * * *